United States Patent [19]

McCormick et al.

[11] Patent Number: 4,798,787
[45] Date of Patent: Jan. 17, 1989

[54] PEPTIDE ANTIBODIES AND THEIR USE IN DETECTING ONCOGENE PRODUCTS

[75] Inventors: Francis P. McCormick, Berkeley; Gail L. Wong, Oakland; Robin Clark, San Leandro; Norman Arnheim, Peidmont; Danute E. Nitecki, Berkeley, all of Calif.

[73] Assignee: Cetus Corporation, Emeryville, Calif.

[21] Appl. No.: 661,909

[22] Filed: Oct. 17, 1984

Related U.S. Application Data

[63] Continuation-in-part of Ser. No. 652,752, Sep. 19, 1984, abandoned.

[51] Int. Cl.[4] .................... G01N 33/531; C07K 7/00; B65D 69/00
[52] U.S. Cl. .......................................... 435/7; 422/61; 435/68; 435/810; 530/350; 530/387; 530/402; 436/501; 436/513; 436/547; 436/813; 436/808
[58] Field of Search ............... 436/813, 547, 543, 501, 436/548; 435/68, 7, 810; 424/86; 260/112 R, 112 B; 530/387, 350, 402; 422/61

[56] References Cited

U.S. PATENT DOCUMENTS

| | | | |
|---|---|---|---|
| 4,535,058 | 8/1985 | Weinberg et al. | 435/6 |
| 4,658,022 | 4/1987 | Knowles et al. | 435/7 |
| 4,699,877 | 10/1987 | Cline et al. | 435/6 |

FOREIGN PATENT DOCUMENTS

| | | |
|---|---|---|
| 0108564 | 5/1984 | European Pat. Off. |
| 0119702 | 9/1984 | European Pat. Off. |
| 8401389 | 4/1984 | PCT Int'l Appl. |
| 8403564 | 9/1984 | PCT Int'l Appl. |
| WO85/00807 | 2/1985 | PCT Int'l Appl. |

OTHER PUBLICATIONS

Alexander, et al., *Nature*, 306, 697–699 (1983).
Tamura, T. et al., *Cell*, 34, 587–596 (1983).
Lerner et al., *Proc. Natl. Acad. Sci. USA*, 78, 3403–3407 (1981).
*The Cancer Letter*, vol. 9, No. 36, pp. 1, 4 and 5 (Sep. 23, 1983).
Shih, T. Y. et al., *Nature*, 287, 686–691 (1980).
McGrath, J. P. et al., *Nature*, 310, 644–649 (1984).
Sweet, R. W. et al., *Nature*, 311, 273–275 (1984).
Gibbs, J. B. et al., *PNAS USA*, 81, 2674–2678 (1984).
Walter, G. et al., *PNAS USA*, 77, 5197–5200 (1980).
Lerner, R. A., *Nature*, 299, 592–596 (1982).
Furth, M. et al., *J. Virol.*, 43, 294–304 (1982).
Gay, N. J. et al., *Nature*, 301, 262–264 (1983).
Weirenga, R. K. et al., *Nature*, 302, 842–844 (1983).
Hand, P. H. et al., *PNAS USA*, 81, 5227–5231 (1984).
Thor, A. et al., *Nature*, 311, 562–565 (1984).
Gallick, G. E. et al., presentation on Sep. 4, 1983 and publication to be submitted entitled "Inhibition of Transformation in a Cell Line Infected with a Temperature Sensitive Mutant of Murine Sarcoma Virus by Cytoplasmic Microinjection of Purified IgG from an Antisera Generated Against a Synthetic v-mos Peptide".

*Primary Examiner*—Christine M. Nucker
*Attorney, Agent, or Firm*—Lisabeth F. Murphy; Gregory J. Giotta; Albert P. Halluin

[57] ABSTRACT

Antibodies exhibit specificity toward single amino acid differences between proteins. These antibodies may be produced by synthesizing a peptide of the appropriate amino acid sequence contained in the protein, immunizing a host with the peptide, and extracting sera from the host to obtain the antibodies. The antibodies and the desired protein are then immunoprecipitated under conditions of partial denaturation to expose the epitope of the protein. The antibodies may be used for diagnostic or therapeutic purposes.

23 Claims, 1 Drawing Sheet

PEPTIDE ANTIBODIES AND THEIR USE IN DETECTING ONCOGENE PRODUCTS

This application is a continuation-in-part application of U.S. Ser. No. 652,752 filed Sept. 19, 1984 now abandoned.

BACKGROUND OF THE INVENTION

1. Field of the Invention

This invention relates to the field of immunology and cancer diagnostics and therapeutics applications. More particularly, it concerns antibodies specific to mutant oncogenes but not to the native proto-oncogene, immunochemicals made from those antibodies, and diagnostic and therapeutic methods which use those immunochemicals.

2. Description of Related Disclosures

Oncogenes are cellular genes that contribute to the neoplastic transformation of cells. See generally Weinberg, R., *Scientific American*, 249: 126-142 (1983). They are altered forms of normal cellular genes, and have been detected in a wide range of human tumors and tumor cell lines. Oncogenes have been detected by transfecting DNA from human tumors or tumor cell lines onto a cell line known as NIH/3T3 cells; cells that take up and express oncogenes from the transfected DNA become altered morphologically, and begin to grow as dense foci. Cells from these foci are able to form tumors when grown in mice (Lane, M. A., Sainten, A. and Cooper, G. M., *Proc Natl Acad Sci USA*, 78: 5185-5189 (1981); and Shilo, B. and Weinberg, R. A., *Nature*, 289: 607-609 (1981)).

The p21 proteins, encoded by members of the ras proto-oncogene family, cause the neoplastic transformation of certain cells in culture when activated through somatic mutation and have been implicated in the generation of a variety of human cancers. The frequency at which ras genes become activated in human tumors may be 20% or higher. Comparison of the structure of the ras oncogenes has revealed that they differ from their non-transforming normal counterparts by point mutations that alter the amino acid sequence of the gene product, p21 protein, at either position 12 or 61 (Parada, L. F., et al., *Nature*, 297: 474-479 (1982); Santos, E., et al., *Nature*, 298: 343-347 (1982); Yuasa, Y. et al., *Nature*, 303: 775-779 (1982)). The most frequently observed mutation leading to the oncogenic activation of the p21 proteins results in the alteration of the amino acid residue at position 12 of the protein to any of several other residues. Marshall, C. J. et al., *Cancer Surveys*, 3: 183-214 (1984).

The p21 protein is known to bind specifically to GTP and to hydrolyze GTP to GDP and inorganic phosphate. Shih, T. Y. et al., *Nature*, 287: 686-691 (1980), McGrath, J. P. et al., *Nature*, 310: 644-649(1984) and Swelt, R. W. et al., *Nature*, 311: 273-275 (1984). In forms of p21 protein that contain a threonine residue at position 59, the phosphate is transferred to this threonine residue by an autophosphorylation reaction. McGrath et al., supra, Gibbs, J. B. et al., *P.N.A.S. USA*, 81: 2674-2678 (1984) and Shih, T. Y. et al., *Nature* (London) 287: 686-691 (1980). The role of these activities in the transforming potential of activated p21 is not yet known. It has been suggested, however, that the portion of the p21 protein surrounding position 12 might be involved in the interaction of p21 protein with GTP. Gay, N. J. et al., *Nature*, 301: 262-264 (1983) and Weirenga, R. K. et al., *Nature*, 302: 842-844 (1983). Furth, M. et al., *J. Virol.*, 43: 294-304 (1982) disclose that both polyclonal sera and monoclonal antibodies directed against various p21 determinants allow GTP binding. The monoclonal antibody Y13-259 does not discriminate between normal and activated p21 protein.

European Patent Publication No. 108,564 to Cline et al. discloses methods for using a probe such as an antibody for detecting the expression product of a c-onc gene, including a ras oncogene, in diagnosing for the presence of malignancy. This publication does not distinguish between the wild-type and mutant form of the polypeptide. U.S. patent application Ser. No. 369,517 filed Apr. 1, 1982 entitled "Expression of Retroviral myc Genes in Human Neoplastic Cells" to T. Papas et al. discloses use of cloned recombinant DNA probes labeled with $^{32}P$ containing the myc oncogene sequences of avian myelocytomatosis virus strain (MC29) to detect human tumor cells. Various blood cells were found to produce elevated amounts of RNA homologous to the myc gene sequences of MC29.

It is known that a peptide segment can be chemically synthesized which corresponds precisely with the amino acid sequence of the region of interest of a protein being studied and the peptide may be coupled to a carried protein and injected into a suitable host to obtain antibodies. For example, Alexander et al., *Nature*, 306: 697-699 (1983) describe two white blood cell proteins (Thy-1) which differ by only a single amino acid and antisera specific thereto induced by short chemically synthesized peptides which span the regions of sequence variation. Tamura, T. et al., *Cell*, 34: 587-596 (1983) disclose the raising of antibodies against synthetic oligopeptides corresponding to the primary structure of pp60$^{src}$ and using the antibodies to immunoprecipitate pp60$^{src}$. Lerner et al., *Proc. Natl. Acad. Sci. USA*, 78: 3403-3407 (1981) disclose use of peptides as vaccines where the peptides correspond to amino acid sequences predicted from the nucleotide sequences of proteins such as the hepatitis B surface antigen. See also Walter, G. et al., *P.N.A.S. USA*, 77: 5197-5200 (1980) and Lerner, R. A., *Nature*, 299: 592-596 (1982). As to the p21 protein, PCT W0/84/01389 published Apr. 12, 1984 to Weinberg et al. discloses the differences between the oncogene of DNA isolated from human bladder cancer cells and its corresponding proto-oncogene. In one type of assay serological reagents are described such as an antibody specific for either p21 protein expressed from the proto-oncogene or oncogene which may be used to detect carcinogenesis. The antibodies may be raised by using a chemically synthesized peptide segment corresponding to the amino acid sequence of the region of interest of the normal or altered peptide sequence being studied.

Hand, H. et al., *P.N.A.S. USA*, 81: 5227-5231 (1984) disclose the generation of monoclonal antibodies using a synthetic peptide reflecting amino acid positions 10-17 of the Hu-ras$^{T24}$ gene product. The antibodies have been shown to react with the ras gene product p21, but were not shown to be specific for activated p21 (altered at position 12) rather than normal p21 protein.

Gallick, G. E. et al. on Sept. 4, 1983 published an abstract for a talk on the inhibition of transformation in a cell line infected with a temperature sensitive mutant of murine sarcoma virus by cytoplasmic microinjection of purified IgG from an antisera generated against a synthetic v-mos peptide. The transformation of the cells was induced by p85$^{gag-mos}$ fusion protein. The antibodies are not shown to be specific for an activated (mutant) oncogene product.

In *Cancer Letter*, Vol. 9 there is published a notice of an NIH RFP proposal for research on monoclonal antibodies to oncogene products of avian and mammalian retroviruses.

One difficulty in product antibodies which are specific to single amino acid differences at position 12 between p21 proteins has been due to the complex structure of the protein, which did not allow antibodies to bind to the particular amino acid epitopic site desired. Another difficulty in producing such antibodies is the unpredictability of whether a given peptide segment will be effective as an immunogen in raising the necessary antibodies. Accordingly, there is a need in the art for an effective peptide immunogen to raise the appropriate antibodies and a method to obtain a modified, relaxed protein with an exposed epitope to which antibodies can bind so that single amino acid differences can be detected. Furthermore, there is a need to determine the mechanism of p21 protein activation so as to develop an effective therapeutic agent to counter the carcinogenic effects thereof.

SUMMARY OF THE INVENTION

In accordance with the present invention, a chemically synthesized peptide of a defined amino acid sequence is used to produce an antibody having specificity for single amino acid differences between proteins. These antibodies are characterized in that they bind selectively to a characteristic marker epitope of an oncogene product, which epitope is not present in the corresponding proto-oncogene product. Preferably, the oncogene product is an activated form of p21 protein and the epitope encompasses position 12 thereof. In this context the word "epitope" refers to the binding site of the oncogene product which recognizes the antibodies herein.

The invention also relates to a partially denatured protein having a characteristic marker epitope which is not exposed in the characteristic undenatured protein, which partially denatured protein is characterized by being denatured sufficiently to expose the epitope. This protein may be prepared by a process wherein the undenatured protein is incubated with a protein denaturing agent under conditions which relax the protein sufficiently to expose the antigenic determinant of the protein to allow access by the antibody but do not substantially inhibit antigen-antibody binding.

The invention also relates to a peptide fragment of the p21 protein useful as an immunogen in raising antibodies binding selectively to a characteristic marker epitope encompassing position 12 of an activated form of p21 protein which peptide comprises a variable amino acid at position 12 of the p21 protein (position 8 of the peptide), a sufficient amount of residues flanking position 12 to define the epitope encompassing position 12, and a cysteine residue in the penultimate position to the C-terminus of the fragment. Preferably, the peptide comprises amino acids 5–17 with the cysteine residue inserted between positions 16 and 17.

In addition, the invention relates to detecting an oncogene product in a cellular sample of a patient which product has a characteristic marker epitope which is not present in the proto-oncogene product and which is not exposed in the undenatured protein which method comprises:

(a) treating the sample with a protein denaturing agent that causes the epitope to be exposed and does not substantially inhibit antigen-antibody binding, (b) incubating the sample with an antibody that binds selectively to said epitope under conditions that permit the binding of said antibody to said epitope, and (c) detecting the presence of immune complexes of the epitope and antibody in the incubate.

Steps (a) and (b) may be carried out simultaneously or sequentially.

The above steps can also be used in a method for detecting a polypeptide, such as sickle cell Hemoglobin, CEA, PAP and HbA$_{1c}$, which is a glycosylated hemoglobin found in the blood of diabetics, having a characteristic marker epitope that is not exposed in an aqueous medium in the undenatured polypeptide.

This invention also relates to a process for inhibiting the binding of an oncogene product to a cellular component necessary for the oncogenic activity of the oncogene product which comprises contacting the oncogene product with an inhibiting agent which binds selectively to a region of the oncogene product containing a characteristic marker epitope of the oncogene product which epitope is not present in the corresponding proto-oncogene product, the inhibiting agent having a direct effect on said binding. In a preferred embodiment, the cellular component is GTP, the inhibiting agent is an antibody, the oncogene product is an activated form of p21 protein and the epitope encompasses position 12 thereof. The inhibiting agent as a composition of matter is also encompassed by this invention.

Another embodiment of the invention is a method for treating cancer comprising contacting one or more cancerous cells with a composition comprising an antibody which binds selectively to a characteristic marker epitope of an oncogene product which is at least partially responsible for the cancer, said epitope not being present in the corresponding proto-oncogene product. One method of contacting the cells is to inject them with the antibody-containing composition.

BRIEF DESCRIPTION OF THE DRAWINGS

FIG. 6 represents photographs of cells transformed with v-Ki-ras p21 which were injected with anti-p21$^{ser}$ antibodies (FIGS. 6a–c) or non-immune normal rabbit immunoglobulin as a control (FIGS. 6d–f). FIGS. 6a and 6d are at 0 hours, FIGS. 6b and 6e are at 24 hours, and FIGS. 6c and 6f are at 36 hours after injection. FIGS. 6a–c show the progression of the cells from the transformed (cancerous) to untransformed (noncancerous, normal) state.

DETAILED DESCRIPTION OF THE PREFERRED EMBODIMENTS

The detection of products of the RAS oncogene in human cells as one specific embodiment in accordance with this invention is based on the ability of certain antibodies to distinguish between proteins which differ by a single amino acid. Antibodies which can distinguish between the normal product of the ras gene (p21 protein) and the mutant activated form by virtue of the single amino acid difference at position 12 or 61 would be used to detect the ras oncogene product by standard techniques such as immunofluorescence, immunoperoxidase staining, immunoprecipitation, ELISA, or Western blotting techniques.

The word "epitope" as used herein refers to the binding site of the oncogene product which recognizes the antibodies of this invention.

The word "antibody" as used herein refers to both polyclonal and monoclonal antibodies. In addition, the term includes whole immunoglobulin as well as antigen binding fragments thereof. The polyclonal antibodies may be produced by injecting a host animal such as rabbit, rat, goat, mouse, etc. with the peptide or peptide segment encoded by the oncogene which carries the amino acid(s) which differentiate the mutant protein from the native protein. The sera are extracted from the host animal and are screened to obtain polyclonal antibodies which are specific to the peptide immunogen. The monoclonal antibodies may be produced by immunizing, for example, mice with the peptide mentioned above. The mice are inoculated intraperitoneally with an immunogenic amount of the peptide and then boosted with similar amounts of the immunogenic peptide. Spleens are collected from the immunized mice a few days after the final boost and a cell suspension is prepared therefrom for use in the fusion.

Hybridomas may be prepared from the splenocytes and a murine tumor partner using the general somatic cell hybridization technique of Kohler, B. and Milstein, C., *Nature* (1975) 256: 495–497. Available murine myeloma lines, such as those from he Salk Institute, Cell Distribution Center, San Diego, Calif., USA, may be used in the hybridization. Basically, the technique involves fusing the tumor cells and splenocytes using a fusogen such as polyethylene glycol. After the fusion the cells are separated from the fusion medium and grown in a selective growth medium, such as HAT medium, to eliminate unhybridized parent cells. The hybridomas may be expanded, if desired, and supernatants may be assayed by conventional immunoassay procedures (e.g., radioimmunoassay, enzyme immunoassay, or fluorescence immunoassay) using the immunizing agent as antigen. Positive clones may be characterized further to determine whether they meet the criteria of the invention antibodies.

Hybridomas that produce such antibodies may be grown in vitro or in vivo using known procedures. The monoclonal antibodies may be isolated from the culture media or body fluids, as the case may be, by conventional immunoglobulin purification procedures such as ammonium sulfate precpitation, gel electrophoresis, dialysis, chromatography, and ultrafiltration, if desired.

As used herein, the term "partially denatured" protein refers to a protein having a characteristic marker epitope which is not exposed in the characteristic undenatured protein and being partially denatured or relaxed sufficiently to expose the epitope site to the antibodies of this invention but at the same time to keep the antibody intact and active in solution and not substantially inhibit antigen-antibody binding. Examples of protein denaturing agents which may be employed for this purpose include urea, deoxycholate, guanidine hydrochloride, sodium dodecyl sulfate, and the like.

The binding of the antibodies to the protein may be enhanced if a sufficiently high concentration of affinity purified antibodies is used. Affinity purification is a technique well known in the art where the antigen peptide is bound to a carrier different from that used for immunization and the antibodies are run through the carrier so as to be purified.

The peptides used to obtain the antibodies for p21 serologically and thus useful as immunogens comprise a variable amino acid at position 12, a sufficient amount of flanking residues to define the characteristic marker epitope to which the antibody binds selectively, and a cysteine residue in the penultimate position to the C-terminal end of the peptide. This peptide may be conjugated to a carrier protein such as keyhold limpet hemocyanin or bovine serum albumin through the cysteine residue before injection into the host.

Figure 1:
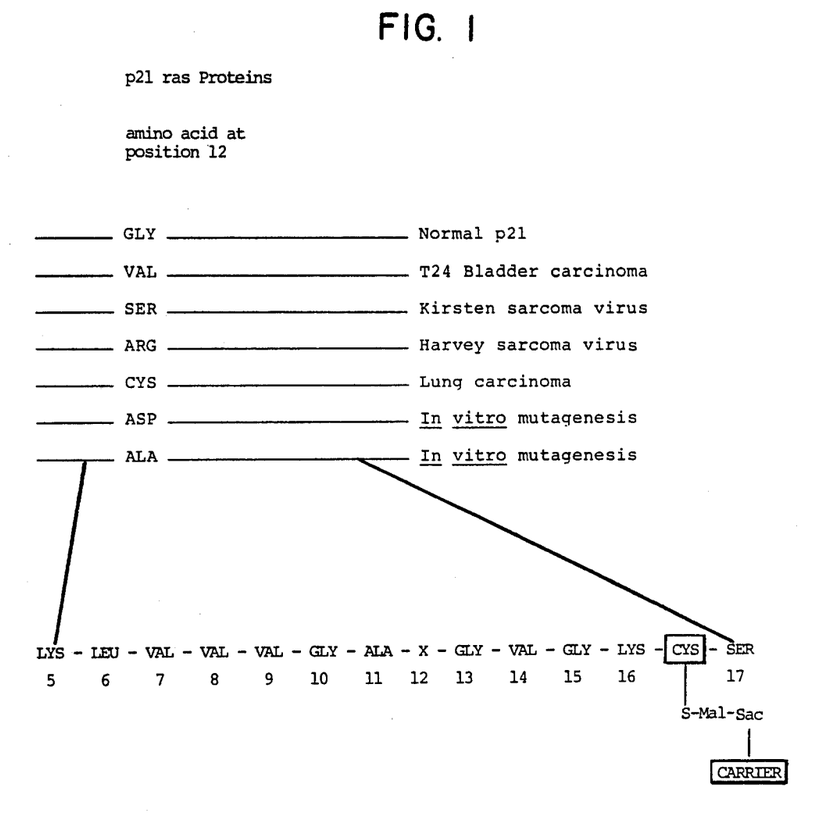
FIG. 1 represents a schematic of the amino acid sequence of the p21 protein surrounding position 12 represented by X. (Position 12 of the protein corresponds to position 8 of the peptide.) A peptide of amino acids 5 to 17, with a cysteine residue inserted between positions 16 and 17, was used as the immunogen to produce the antibodies of the examples herein.

The peptide fragment must have enough amino acid residues to define what is the epitope of the protein segment being detected but must not be so large as to have a definite conformation different from that of the protein being detected. If the peptide fragment is too short the fragment will be found in irrelevant other proteins and it might be physically buried in the immunizing carrier protein. The cysteine residue, penultimate to the C-terminus, is used to link the carrier protein to the peptide fragment. FIG. 1 depicts one useful fragment for p21 protein.

The oncogene products which may be employed herein are structurally modified (mutant) oncogene products different from the proto-oncogene product. Examples of such oncogene products include the cellular gene products consisting of ras oncogene products (p21$^{c-H-ras}$ and p21$^{c-K-ras}$), the myc oncogene product (p58$^{c-myc}$), the sis oncogene product (PDGF B-chain) and the like. Preferably the oncogene product herein is an activated form of p21 protein. The term "activation" as applied to a protein product signifies a change in the DNA which in turn alters the protein so as to cause an oncogenic transformation.

The peptide antisera against p21 protein representative of the antibodies of this invention may be prepared by the following technique.

Six synthetic peptides corresponding to amino acids 5 to 17 of the p21 RAS gene product are prepared by replacing the normal amino acid glycine found at position 12 of the native p21 protein with each possible amino acid which can arise from a single base change in the codon at this position. These amino acids are serine, arginine, cysteine, valine, alanine, and aspartic acid. FIG. 1 depicts the amino acid sequence of the relevant part of the p21 protein from positions 5 to 17. The peptides which are prepared are tetradecapeptides which must contain an additional cysteine residue penultimate to the C-terminal serine end which will couple to the carrier protein. The effect of each amino acid change at position 12 is indicated in the right hand column. The peptides may be synthesized by the solid phase synthesis method known in the art and described by Merrifield in Example 1 using an automated SAM Peptide Synthesizer and a manual solid phase synthesis instrument "Peptider". The peptide is cleaved from the resin used in the synthesis by liquid hydrogen fluoride and purified by column chromatography. After synthesis the peptide is covalently coupled through the cysteine residue at the C-terminal end to a carrier protein such as keyhole limpet hemocyanin (KLH) or bovine serum albumin (BSA) and injected into rabbits.

Antibody titers are measured using an ELISA protocol in which Immunol ® brand polystyrene test plates are coated with each peptide coupled covalently to another carrier protein which is different from the carrier protein used in the immunization peptides so that screening of the antibodies can be conducted. Separation of position 12—specific antibodies from non-specific antibodies is achieved by passing sera over an affinity column to which a peptide BSA complex is covalently attached. In the case of antiserum raised against peptide with serine at position 12, the peptide used in the affinity column has glycine at this position. Antibodies which fail to bind to this affinity column have specificity for serine at position 12, as judged by ELISA.

The anti-peptide antibodies produced are tested for their ability to distinguish among amino acid substitutions at position 12 in whole proteins using immunoprecipitation under conditions of partial denaturation of the p21 protein. Thus, the antibodies and protein are combined and incubated in the presence of a protein denaturing agent buffer containing SDS and/or deoxycholate at pH 7.5–8.0 for 0.5–1 hour. More generally, protein denaturation conditions are well known, but for purposes of this invention are conducted at a physiological pH, for example, for p21 a pH of about 7.5 to 9, preferably 8, using a concentration of SDS of about 0.05 to 0.10% by weight and/or of deoxycholate of about 0.1–1% by weight, preferably 0.5 to 1%, for a time period of 0.5 to 1 hour. All of these conditions will depend, for example, on the particular oncogene product being employed and the purity of the antibody.

After immunoprecipitation the immune complexes are collected on Protein A Sepharose, washed and analyzed by SDS-PAGE.

The antibodies herein may be used as immunochemicals for both therapeutical and diagnostic purposes. For therapeutic use the antibody, attached to a carrier, could be incorporated into a tumor to reverse the malignant effect thereof.

Antibodies capable of distinguishing RAS oncogenes from their normal counterparts by virtue of single amino acid differences in the gene product (p21 protein) may be applied to diagnostic detection of malignant cells in many clinical situations. For example, the presence of RAS oncogenes may have prognostic significance in determining the course of therapy for a particular type of cancer. In another situation, detection of RAS oncogenes in malignant cells could facilitate detection of these cells amongst a large number of normal cells, and thus be a useful tool in monitoring the course of the disease, as well as in its early detection. The primary diagnostic uses for the anti-p21 antibodies may be immunohistochemical to detect any cancer involving the c-ras mutant or as a serum marker.

The immunochemical derivatives of the antibodies of this invention that are of prime importance are labeled (e.g., radiolabeled, enzyme-labeled, or fluorochrome-labeled) derivatives in which the label provides a means for identifying immune complexes that include the labeled antibody. Whether the antibody would be workable in a therapeutic format such as an immunotoxin depends on what protein is the antigen.

The labels that are used in making labeled versions of the antibodies include moieties that may be detected directly, such as fluorochromes and radiolabels, as well as moieties, such as enzymes, that must be reacted or derivatized to be detected. Examples of such labels are $^{32}P$, $^{125}I$, $^{3}H$, $^{14}C$, fluorescein and its derivatives, rhodamine and its derivatives, dansyl, umbelliferone, luciferin, 2,3-dihydrophthalazinediones, horseradish peroxidase, alkaline phosphatase, $\beta$-galactosidase, lysozyme, and glucose-6-phosphate dehydrogenase. The antibodies may be tagged with such labels by known methods. For instance, coupling agents such as dialdehydes, carbodiimides, dimaleimides, bis-imidates, bis-diazotized benzidine and the like may be used to tag the antibodies with the above-described flurorescent, chemiluminescent, and enzyme labels.

The antibodies and labeled antibodies may be used in a variety of immunoassay procedures to detect the presence of cancer in a human patient or to monitor the status of such cancer in a patient already diagnosed to have it. When used to monitor the status of a cancer a quantitative immunoassay procedure must be used. In such monitoring, assays are carried out periodically and the results compared to determine whether the tumor burden of the host has increased or decreased. Common assay techniques that may be used include direct and indirect assays. Direct assays involve incubating, in vivo and in vitro, a tissue sample or cells from the host with one or more labeled antibodies. If the sample includes cancer cells, the labeled antibodies will bind to those cells. After washing the tissue or cells to remove unbound labeled antibodies, the tissue sample is read for the presence of labeled immune complexes. In indirect assays the tissue or cell sample is incubated with one or more unlabeled antibodies. The sample is then treated with a labeled antibody against the antibody (e.g., a labeled anti-rabbit antibody), washed, and read for the presence of labeled ternary complexes.

In an in vitro assay for detecting cancer in a body fluid sample, the sample may be incubated with an antibody herein against the protein which is unlabeled, preferably one where the antibody is immobilized on a solid support. The sample is incubated before, during or after this incubation with another antibody which is labeled. After washing, the sample is read for the presence of labeled complexes. The two antibodies employed may both be directed against p21 (different epitopes) or the second antibody may be against the first antibody.

In addition, the antibodies may be used in a competitive RIA format.

For diagnostic use the antibodies will typically be distributed in kit form. These kits will typically comprise: the antibody or antibodies in labeled or unlabeled form in suitable containers, a denaturing buffer, reagents for the incubations and washings if necessary, a labeled anti-rabbit antibody if the kit is for an indirect assay, and substrates or derivatizing agents depending on the nature of the label. Human cancer antigen controls and instructions may also be included. In addition, the antibodies in the kit may be affinity purified.

The high specificity of the antibodies herein for a particular oncogene product, taken together with their ability to modulate the biochemical activity of the oncogene product makes these antibodies very useful probes for studying the structure of oncogene products and their role in oncogenesis of both in vitro and in vivo. Potentially, the antibodies could be used to control the oncogene product activity in complex in vitro systems and to probe the interactions of the oncogene product with other cellular components.

The antibodies herein may also be used in cancer therapeutics. For example, they, as well as other suitable pharmaceutical formulations or drugs, may be used as an inhibiting agent in a process for inhibiting the binding to an oncogene product of a cellular component necessary for the oncogenic activity of the oncogene product. In such process the oncogene product such as those described above is contacted with the inhibiting agent, which must be capable of inhibiting the binding of the oncogene product to the cellular component. The specific inhibiting agent employed will depend, e.g., on the oncogene product and cellular component involved. If the oncogene product is a mutant of the proto-oncogene product, the inhibiting agent will bind selectively to a characteristic marker epitope of the oncogene product which epitope is not present in the corresponding proto-oncogene product. This inhibiting agent also must exert a direct effect on the binding of the cellular component to the oncogene product. This direct effect may be that the epitope includes at least a portion of the site where the cellular component binds the oncogene product or may be that the inhibiting agent binds or acts at a distance from the epitope and alters the binding by disturbing the tertiary structure of the oncogene product. This invention is not limited to any particular theory regarding how the inhibiting agent acts on the binding.

The cellular component which is required for the functioning of the oncogene product may be, for example, proteins, lipids, carbohydrates, nucleic acids, metabolites such as nucleotides, e.g., ATP, CTP, GTP, UTP, and the like. The particular component of the cell which is required for the function of the oncogene product will depend on the product involved. Thus, for example, for the activated p21 protein, the cellular component will be GTP, which binds to the activated p21 protein so as to render it carcinogenic. Other proteins will have specificity for the same or different cellular components.

Preferably the inhibiting agent herein is an antibody, which may be an affinity purified polyclonal antibody, and the oncogene product is the activated p21 protein with its characteristic marker epitope encompassing position 12 of that protein.

The antibody herein may be used specifically in a process for treating patients having cancer where one or more of the cancerous cells of the patient are contacted with a composition comprising an antibody which binds selectively to a characteristic marker epitope of an oncogene product which is at least partially responsible for the cancer, the epitope not being present in the corresponding proto-oncogene product. The antibody may be contacted with the cells by microinjection or may be attached to a carrier molecule which will allow the antibody to pass through the cell membrane freely with no injection necessary. The carrier molecule for this purpose may be hydrophobic and may be analogous or possibly the same as the B-chain of ricin which pulls the active A-chain of ricin through the cell membrane. Preferably the oncogene product for this process is an activated form of p21 protein with its marker epitope encompassing position 12 of the protein.

The invention is further illustrated by the following examples, in which all percentages are by weight and all temperatures are provided in degrees Centigrade, unless otherwise noted.

EXAMPLE 1

A. Peptide Syntheses

Tetradecapeptides shown at the bottom of FIG. 1 where X is gly, val, ser, arg, cys, asp or ala and containing an additional cysteine residue penultimate to the C-terminal ser end were synthesized by the solid phase synthesis method using automated SAM Peptide Synthesizer (Biosearch Corp.) and the manual solid phase synthesis instrument "Peptider" (Peninsula Laboratories).

The solid phase synthesis method as used herein is described by Merrifield, R. B., *Adv. Enzymol. Relat. Areas Mol. Biol.*, 32: 221–296 (1969) and in "The Chemistry of Polypeptides" (P. G. Katsoyannis, ed.), pp. 336–361, Plenum, New York (1973). Laboratory aspects of the technique are described by Stewart, J. M. et al., "Solid Phase Peptide Synthesis", Freeman, San Francisco, Calif. (1969).

The synthesis herein was performed using commercially available N-t-butyloxycarbonyl-L-serine (O-benzyl ether) covalently attached to a polystyrene resin by benzyl ester bond as the C-terminal amino acid. The synthesis was a repetitive cyclic method of deprotection of the protecting group from the α-amino group by trifluoroacetic acid, neutralization of the trifluoroocetate salt by diisopropylethylamine and coupling of the next N-t-butyloxycarbonyl-protected amino acid by a carbodiimide. All amino acid derivatives and all reagents used are commercially available.

Extensive washing of the resin was necessary during the synthesis, i.e., after each reaction (deprotection, neutralization and coupling). The resin was washed with appropriate organic solvents such as dichloromethane, dioxane and dimethyl formamide.

Cysteine does not naturally occur in the 16 or 17 positions from the amino terminus in the p21 protein, but it was incorporated between these positions to enable subsequent attachment of the peptides to protein carriers necessary for immunization.

The peptide was cleaved from the resin by liquid hydrogen fluoride with a small amount of anisole added. The cleaved peptide was extracted from the resin into 2N aqueous acetic acid and lyophilized. One gram of air-dried peptide-resin yielded 339 mg of crude peptide.

For purification, the peptide (100 mg) was treated with dithiothreitol (30 mg) in 5 ml of 2N acetic acid solution and chromatographed on a LH Sephadex column, 150 ml bed volume, in 2N acetic acid. The fractions containing the major portion of the peptide were combined and lyophilized. A total of 56 mg of the peptide was recovered.

The homogeneity of the peptides was investigated by reversed phase HPLC and by the amino acid composition of the hydrolyzates of the peptides.

The conjugation of these peptides to keyhole limpet hemocyanin (KLH) or bovine serium albumin (BSA) was achieved via the sulfhydryl group in the cysteine residue. A heterobifunctional crosslinking reagent, N-maleimido-6-amino caproyl ester of 1-hydroxy-2-nitro-benzene-4-sulfonic acid sodium salt, was prepared by the following procedure.

One molar equivalent (2.24 g) of 4-hydroxy-3-nitrobenzene sulfonic acid sodium salt (HNSA) was mixed together with one molar equivalent (2.06 g) of dicyclohexylcarbodiimide and one molar equivalent (2.10 g) of N-maleimido-6-aminocaproic acid in 25 ml of dimethylformamide (DMF) at room temperature overnight. A white precipitate of dicyclohexyl urea was formed. The precipitate was filtered and 300 ml diethyl ether was added to the mother liquor. After about 10 minutes to 4 hours a gummy solid precipitate from the mother liquor was formed. This solid was found to contain 58% of active HNSA ester and 42% of free HNSA.

The analysis consisted of dissolving a small amount of the precipitate in phosphate buffer at pH 7.0 and measuring absorbance at 406 nm; this reading provides the amount of unreacted free HNSA which is the contaminating material in the HNSA ester preparation. Addition of very small amounts of concentrated strong base (such as 5N NaOH) instantly hydrolyzed the ester formed and a second reading was taken. Subtraction of the first reading from the second yields the amount of ester in the original material. The solid was then dissolved in DMF and placed on a LH20 Sephadex column and eluted with DMF so that the ester was separated from the contaminating free HNSA. The progress of purification was monitored by thin layer chromatography using eluting solvents of chloroform, acetone and acetic acid (6:3:1 vol/vol). The product was positively identified as mal-sac HNSA ester by its reactivity with amines. The yield of the pure ester was estimated to be approximately 30% of theoretical; the purified material consisted of 99% ester.

The ester thus obtained was found to dissolve fully in water and was found to be stable in water for several hours, provided no nucleophiles were added. When placed in 1N ammonia the ester produced the corresponding amide with a portion hydrolyzed to free acid. The purified ester was found to be stable for extended periods when stored dessicated.

About 0.5 mg of the purified mal-sac HNSA ester was dissolved in 1 ml of distilled water. A 10 $\mu$l aliquot of this solution was diluted into 1 ml of 10 mM phosphate buffer at pH 7.0. The absorbance at 406 nm was used to calculate the concentration of free HNSA as described above. When 50 $\mu$l of 4.8N sodium hydroxide solution was added to the diluted aliquot of ester and mixed, the absorbance of the solution at 406 nm increased significantly, indicating that the hydroxide nucleophile rapidly hydrolyzed the ester to component acid and free HNSA anion.

The difference between the post-base and initial free HNSA concentration represents the concentration of ester. From the actual concentration of ester and protein amino groups the amount of ester to be added to the protein solution to achieve the desired degree of substitution can be calculated.

The purified HNSA ester was then reacted with BSA as follows (the reaction with KLH was similar to this procedure):

A total of 22 mg (20 $\mu$moles) of BSA (of molecular weight 66,296) was dissolved in 2.0 ml of 0.1M phosphate buffer at pH 7.5 to yield a total amine concentration of $1.0 \times 10^{-2}$ moles per liter (assuming 59 lysines/BSA molecule). A calculated amount (11 mg, $2.35 \times 10^{-5}$ moles) of the above-prepared mal-sac HNSA ester (97.7% pure) in powder form was dissolved in 2.0 ml of the BSA solution. The reaction was carried out at room temperature. Ten $\mu$l aliquots were removed from the solution at timed intervals and were each diluted into 1.0 ml of 0.01M phosphate buffer at pH 7.0. The spectrum of each diluted aliquot was recorded using a Hewlett-Packard spectrophotometer and the absorbance at 406 nm measured. A total of 50 $\mu$l of 4.8N NaOH was then added to each aliquot, each aliquot was mixed and its spectrum retaken and the absorbance at 406 nm measured. The results appear in Table 1.

TABLE 1

| Time (minutes) | Without NaOH | | With NaOH | | | |
|---|---|---|---|---|---|---|
| | Absorbance Peak at 406 nm | Concentration of NHSA (moles/l) | Absorbance Peak at 406 nm | Concentration of HNSA (moles/l) | Concentration of Ester (moles/l) | Percent Ester Remaining in Solution |
| 0 | 0.046 | $1.03 \times 10^{-5}$ | 0.648 | $1.66 \times 10^{-4}$ | $1.56 \times 10^{-4}$ | 94.0 |
| 5 | 0.095 | $2.44 \times 10^{-5}$ | 0.547 | $1.40 \times 10^{-4}$ | $1.16 \times 10^{-4}$ | 82.9 |
| 9 | 0.112 | $2.87 \times 10^{-5}$ | 0.516 | $1.32 \times 10^{-4}$ | $1.03 \times 10^{-4}$ | 78.3 |
| 14 | 0.147 | $3.77 \times 10^{-5}$ | 0.579 | $1.49 \times 10^{-4}$ | $1.11 \times 10^{-4}$ | 74.5 |

From the absorbance at 406 nm before and after addition of base the concentration of ester remaining and the percent ester reacted were determined for the reaction mixtures. The results show that the reaction rate is essentially linear over a 15 minute period.

At 15 minutes of reaction time the reaction was stopped by applying the reaction mixture to a PD10 desalting Sephadex G-25 column (Pharmacia, Inc.) equilibrated with 0.1M phosphate buffer at pH 6.0. It was found that $2.6 \times 10^{-3}$ moles/l of the ester had reacted and thus 25.9% of the 59 epsilon-amino groups of BSA were presumably substituted. Thus, the product contained 16 mal-sac groups per molecule.

The product of the first reaction, mal-sac-BAS (or mal-sac-KLH), was isolated by applying the reaction mixture to a PD10 desalting Sephadex G-25 column equilibrated with 0.1M phosphate buffer at pH 6.0. The column was eluted with 0.1M phosphate buffer in 1.0 ml fractions. The column elution was followed by monitoring the absorbance spectrum, and peak fractions containing the mal-sac BSA were pooled. 18 mg of cysteine-containing tetradecapeptides synthesized as described above were added and the pooled mixture was stirred at room temperature overnight. The conjugates were subjected to extensive dialysis against distilled water and lyophilization, and in some cases were analyzed for changes in amino acid composition.

B. Preparation of Antisera

New Zealand white rabbits were immunized with ½ mg of the KLH derivatives of the peptides by peripheral lymph node injection in Freunds Complete Adjuvant followed two weeks later by a ½ mg subcutaneous (sub. q.) injection in Freunds Incomplete Adjuvant. Three additional ½ mg sub. q. injections were given at three week intervals. One month later three intravenous boosts of ½ mg each were given 4 days apart and the serum sample used in these studies was taken 11 days later.

C. ELISA Assays to Measure Antibody Titres 96 well Immulon ® brand polystyrene test plates were coated overnight at 4° C. with 50 $\mu$l (per well) of a 250 $\mu$gm/ml solution of the appropriate BSA-peptide conjugate. After washing the wells with PBS-Tween, dilutions of the antisera to be tested were added and incubation was carried out for 2-3 hours at room temperature. After further PBS-Tween washes Goat anti-rabbit IgG (peroxidase conjugate) at a dilution of 1/1000 was added and incubated for one hour at room temperature. Following further washes with PBS-Tween the peroxidase substrate was added (ABTS, Sigma), and readings were taken 30 minutes later.

D. Affinity Purification of Antibodies

Separation of position 12-specific antibodies from non-specific antibodies was achieved by passing the sera over a Reacti-Gel affinity column to which a peptide BSA conjugate was covalently attached. In the case of antiserum raised against the peptide with serine at position 12, the peptide used in the affinity column had glycine at this position. Antibodies which failed to bind to this affinity column had specificity for serine at position 12, as judged by ELISA. The flow-through from this column was passed over a second column to which the peptide with serine at position 12 was covalently attached. Antibodies which bound to this column were eluted with 50 mM glycine.HCl, pH 2.5, dialyzed against 1/20 X phosphate buffered saline (PBS), and concentrated by centrifugation under vacuum to a final concentration of 10 mg/ml in PBS.

E. Immunoprecipitation of p21 Protein with Antibodies

Figure 2:
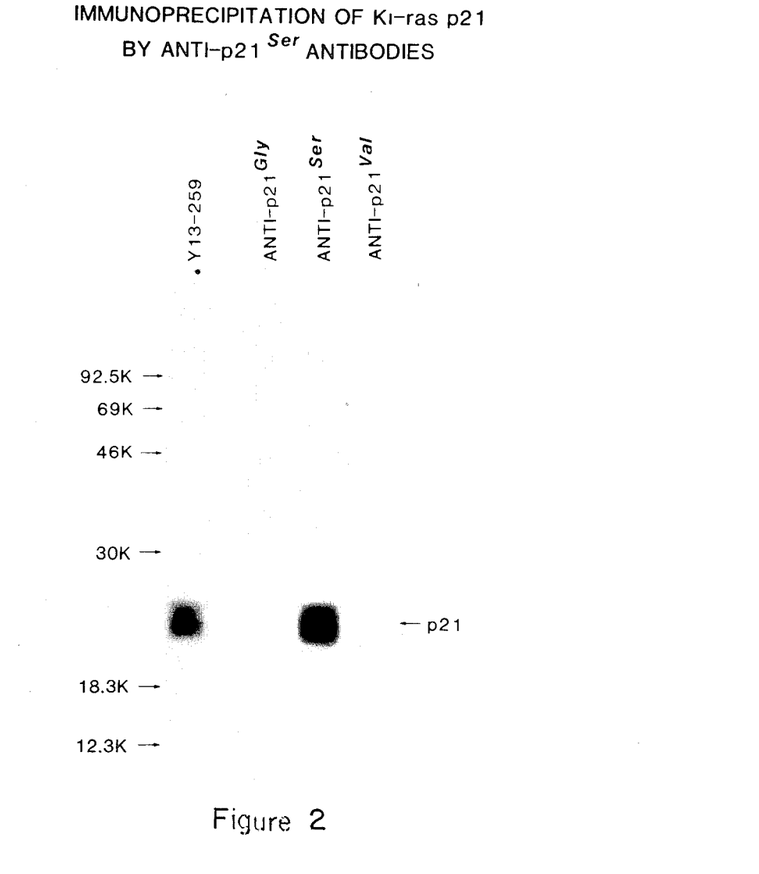
FIG. 2 represents autoradiograms of the SDS-PAGE analysis of immune complexes of affinity purified anti-p21 sera directed against gly, ser or val at position 12 and the v-Ki-ras p21 protein containing a serine moiety expressed by *E. coli*. The lane on the left represents a control.

The ability of the anti-peptide antisera to immunoprecipitate p21 protein is shown in FIG. 2, which is an autoradiogram of the SDS-PAGE gel.

In this example the antibody was used to immunoprecipitate a form of p21 protein which is known to contain serine at position 12. This protein is a E. coli expressing v-Ki-ras p21 protein (produced using a plasmid pINIII-ras which was constructed by and was a gift from M. Inouge of SUNY at Stony Brook, N.Y. in which transcription was directed by the lac promoter—see Masui, Y. et al., in Experimental Manipulation of Gene Expression, M. Inouge, ed., Academic Press, N.Y., pp 15–32 (1983). Expression of this protein was induced by treatment of the cultures with 2 mM isopropylthiogalactoside (IPTG). Cell pellets were resuspended in 50 mM glucose, 25 mM Tris.HCl pH 8.0, 10 mM EDTA, 2 mg/ml lysozyme, and 0.01% aprotinin, and were then incubated for 30 minutes at 4° C. Triton X-100 was added to 1% concentration for 5 additional minutes. Following a 10-minute 15,000×g spin, the supernatant was spun for an additional 2 hours at 150,000×g to prepare the cleared lystate. One hundred-$\mu$l samples of the cleared cell lysate were incubated with 40 $\mu$Ci $^{32}$P gamma-labeled guanosine triphosphate (GTP) for 30 minutes at 37° C. Twenty-five $\mu$l aliquots of these extracts were incubated with either 0.2 $\mu$g of a control monoclonal antibody Y13-259 described below, 10 $\mu$l of anti-p21$^{ser}$, 10 $\mu$l of anti-p21$^{val}$, or 10 $\mu$l of anti-p21$^{gly}$ (the latter sera raised against peptides identical to that shown in FIG. 1 where X is valine or glycine, respectively). This incubation was carried out in the presence of a partial denaturing buffer consisting of 0.05% SDS, 2 mM dithiothreitol, 0.5% NP40, 50 mM Tris.HCl, pH 8.0, 120 mM NaCl. After one hour the immune complexes were collected on 10 $\mu$l of Protein A Sepharose beads, which, in reactions utilizing Y13-259 and rat IgG, had been precoated with affinity-purified goat anti-rat IgG. Immune complexes were washed with 0.5% NP40, 1M LiCl, 50 mM Tris.HCl, pH 8.0, 120 mM NaCl, and analyzed by SDS-PAGE. The gel thus obtained was dried on a piece of paper and then laid on a piece of film by standard autoradiographic procedures to obtain FIG. 2, which shows the results of these analyses. The control on the left is the monoclonal antibody Y13-259 (a gift from Mark Furth of Sloan Kettering Institute, First Ave., New York, N.Y.) which is known to immunoprecipitate this particular form of p21 protein. Furth, M. et al., J. Virol., 43: 294–304 (1982). FIG. 2 shows that the only serum of the three tested which reacted with this form of p21 protein was that raised against the serine-containing peptide. Thus, the antibodies are able to distinguish between single amino acid changes in the protein.

Figure 3:
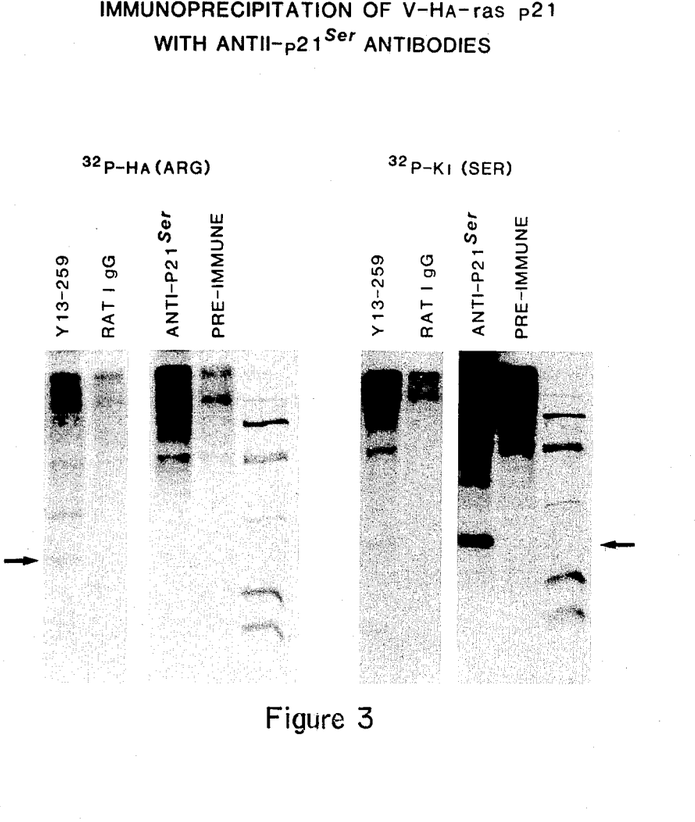
FIG. 3 represents autoradiograms of the SDS-PAGE analysis of two p21 proteins with ser and arg amino acid substitutions at position 12 from transformed mammalian cells immunoprecipitated with anti-p21$^{ser}$ antibodies. The two lanes on the left of each group are controls and the lane farthest right is the M.W. standards. The lane second from the right labeled pre-immune is the immunoprecipitated rabbit sera before injection.

In another experiment on immunoprecipitation, mammalian cells transformed by either Harvey sarcoma virus DNA (v-Ha ras) or Kirsten sarcoma virus DNA (v-Ki-ras) were used as sources of the p21 antigen. The former cells (a Rat-2 fibroblast line designated KP6) were a gift from Dr. Mike Kreigler of Fox-Chase Cancer Institute, 7701 Burholme Ave., Philadelphia, PA 19111. The latter cells (K-balb) were obtained from the American Type Culture Collection, 12301 Parklawn Drive, Rockville, MD 20852-1776 as ATCC CCL 163.3 (K-234) and described as Kirsten murine sarcoma virus-transformed Balb/3T3, nonproducer. The latter culture was infected with an ecotropic strain of murine leukemia virus to increase expresesion of v-Ki-ras p21. Monolayers of these transformed cells were metabolically labeled with 2 $\mu$Ci of carrier-free inorganic phosphate per 50 mm plate for 4 hours at 37° C., and extracts were prepared in PBS plus 1% Triton X-100 as surfactant, 0.5% deoxycholate as detergent and 0.01% aprotinin as protease inhibitor. Aliquots of these extracts, which contained the v-Ha-ras p21 (with arginine at position 12) or the v-Ki-ras p21 (with serine at position 12), were reacted for 1 hour at room temperature with 0.25 $\mu$g of Y13-259 monoclonal antibody as control, 0.25 $\mu$g of rat IgG, 5 $\mu$g of pre-immune rabbit serum, or 5 $\mu$g of affinity-purified anti-p21$^{ser}$ antiserum (i.e., the anti-p21$^{ser}$ antibodies which were raised against the peptide with serine at position 12 and were separated from position 12 non-specific antibodies using affinity chromatography as described above (where the peptide used in the affinity column had glycine at the amino acid corresponding to position 12 of p21 protein)). The reaction was carried out using the same partially denaturing conditions described above except that the amount of SDS used was 0.1% rather than 0.05% by weight. The immune complexes were collected on Protein A Sepharose, washed, and analyzed by SDS-PAGE using standard autoradiographic procedures as described for FIG. 2. In FIG. 3, which is the autoradiogram, the control on the far right lane is the molecular weight standard, the control lane next to it is the rabbit sera prior to immunization, and the two lanes on the left of each group are, respectively, the monoclonal antibody Y13-259 described above and Rat IgG as controls. FIG. 3 illustrates that the serum raised against the serine-containing peptide was able to immunoprecipitate the p21 of Kirsten sarcoma virus, which has serine at position 12, but was unable to immunoprecipitate Harvey sarcoma virus p21, which has an arginine residue at this position. The same antiserum was not found to react with p21 proteins containing glycine at position 12. In the absence of SDS or deoxycholate partial denaturation the immunoprecipitation did not occur.

The results herein indicate that the position 12 amino acid residue (serine) is included in the anti-p21$^{ser}$ epitope. In addition, anti-p21$^{ser}$ did not react with p21 containing glycine (normal p21) at position 12 from the cell line hs242 described by Yuasa, Y. et al., Nature, 303, 775-779 (1983).

F. Inhibition of Autophosphorylation of v-Ki-ras p21 by anti-p21$^{ser}$ Antibodies The anti-p21$^{ser}$ antibodies were also found to inhibit autophosphorylation of the v-Ki ras oncogene product in in vitro experiments, indicating that the portion of p21 protein surrounding position 12 is involved in the interaction of p21 protein with GTP.

Figure 4:
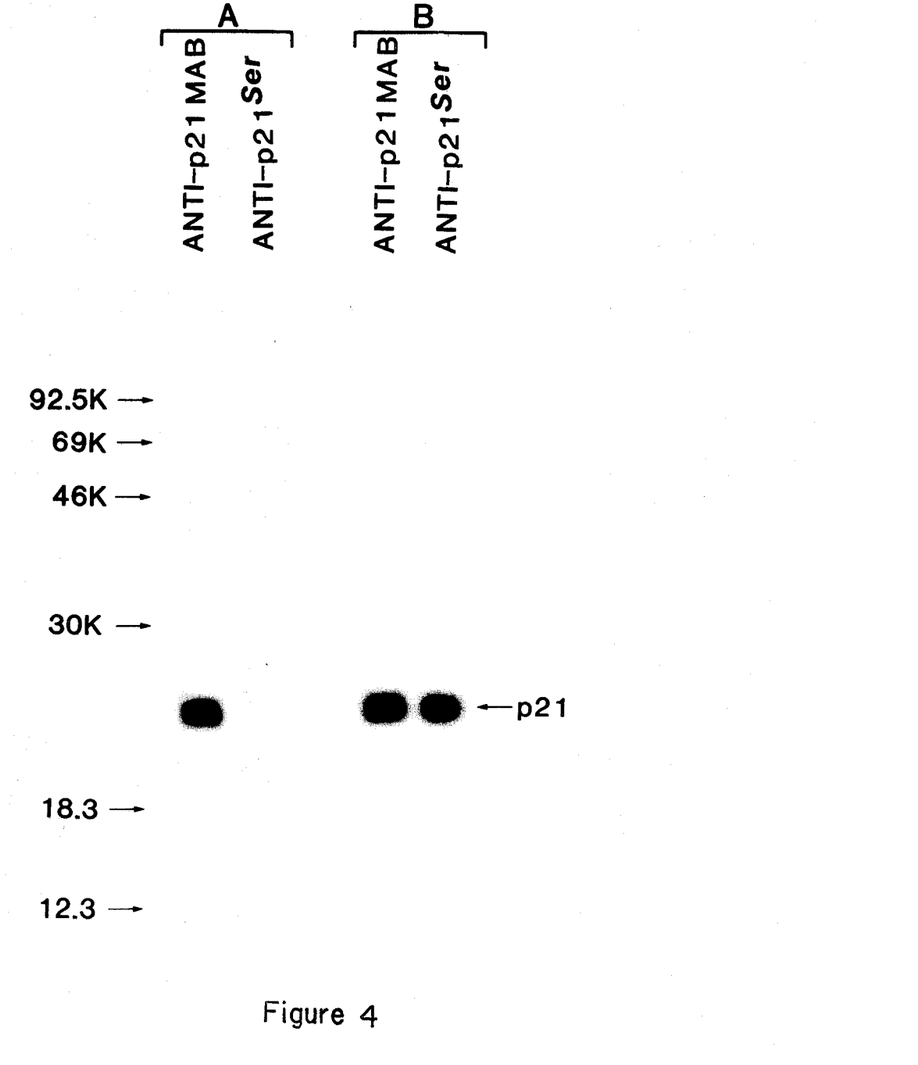
FIG. 4 represents autoradiograms of the SDS-PAGE analysis of the immune complexes labeled with gamma labeled GTP of *E. coli* expressing v-Ki-ras p21 with either anti-p21$^{ser}$ or monoclonal antibody Y13-259 (designated in the figure as anti-p21MAB) which is known to fail to inhibit GTP hydrolysis by p21 protein. The lanes designated A represent immunoprecipitation prior to phosphorylation and the lanes designated B represent immunoprecipitation after phosphorylation.

An extract from E. coli expressing v-Ki-ras p21 was immunoprecipitated with either anti-p21$^{ser}$ antibodies, as described above, or Y13-259 monoclonal antibody, and the resulting immune complexes were incubated with 10 $\mu$Ci$^{32}$P gamma-labeled GTP for 30 minutes at 37° C. The immune complexes were collected on Protein A Sepharose, washed, analyzed by SDS-PAGE, and subjected to standard autoradiographic methods as described above. The result was that no autophosphorylation occurred in the anti-p21$^{ser}$ immune complex. In contrast, E. coli-produced p21 immunoprecipitated by Y13-259 monoclonal antibody was actively phosphorylated. See FIG. 4A, which is an autoradiogram of both materials. Pre-labeled p21 immunoprecipitated efficiently under the conditions used, i.e., the lack of autophosphorylation was a result of inhibition of enzyme activity and not failure of the serum to bind p21.

A total of 25 $\mu$l of an extract from E. coli expressing v-Ki-ras was first adjusted to 100 mM NaCl, 5 mM MgCl$_2$ and 50 mM Tris.HCl (pH 8.0), and the resulting immune complexes were incubated with 10 $\mu$Ci of gamma-labeled GTP for 30 minutes at 37° C. Immunoprecipitation with anti-p21$^{ser}$ or Y13-259 monoclonal antibody was then carried out under conditions identical to those described above. The immunoprecipitates were run on SDS-PAGE and subjected to autoradiography as described above to yield FIG. 4B.

FIG. 4A shows that the GTP-dependent autophosphorylation of E. coli-produced p21$^{ser}$ antibody was completely eliminated after immunoprecipitation by anti-p21$^{ser}$ antibodies. In contrast, p21 protein was efficiently autophosphorylated after immunoprecipitation with a control monoclonal antibody Y13-259, which is known to fail to inhibit GTP hydrolysis by p21 protein. When the p21 was phosphorylated prior to immunoprecipitation, however, (FIG. 4B), both antibodies were seen to precipitate labeled p21 protein efficiently.

Thus, binding of anti-p21$^{ser}$ to v-Ki-ras p21 resulted in inhibition of p21 autophosphorylation. The most likely explanation of this result is that antibodies compete with GTP for binding at the same site.

G. Inhibition of GTP Binding by Anti-p21$^{ser}$ Immunoglobulin

Figure 5:
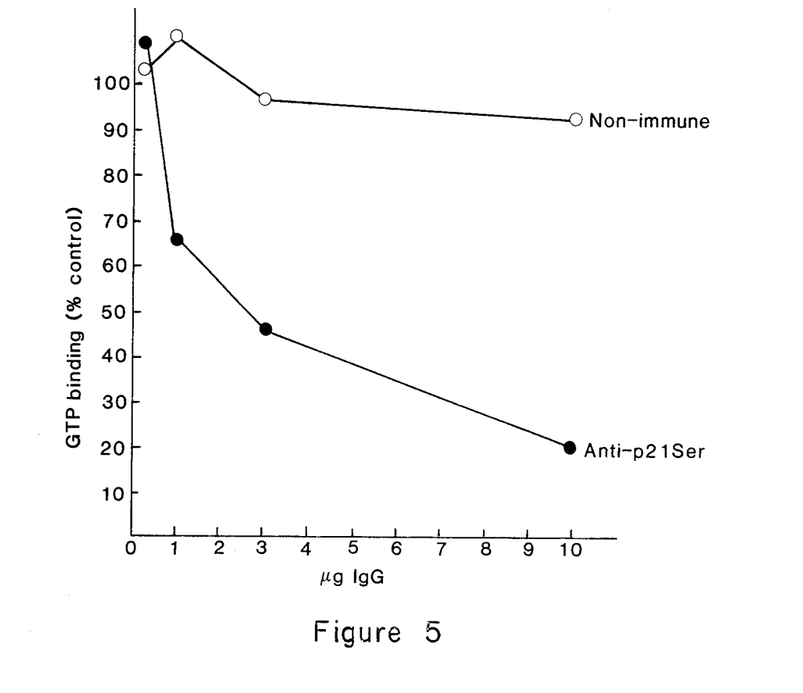
FIG. 5 represents a plot of GTP binding to the p21 protein as a percent of the control (with no added antibody) versus the amount of either non-immune normal rabbit immunoglobulin or anti-p21$^{ser}$ antibodies which are added to the v-Ki-ras p21 immunoprecipitated with Y13-259.

To confirm the above result and determine whether the antibody blocked the binding of GTP rather than the transfer of phosphate to the threonine at position 59, the applicants tested the ability of anti-p21$^{ser}$ antibodies to block directly the binding of $\alpha$-$^{32}$PdGTP to p21 protein in a monoclonal antibody-linked immunoabsorption assay.

v-Ki-ras p21 produced in E. coli was immunoprecipitated with 2 $\mu$l of monoclonal antibody Y13-259 coupled to Reactigel beads obtained from Pierce Chemical Co. Immune complexes were washed with 0.5% NP40, 50 mM Tris.HCl, pH 8.0, 1M LiCl and 120 mM NaCl. The washed complexes were incubated for 1 hour at 4° C. in 0.5% Triton X-100, 0.5% deoxycholate, 150 mM NaCl, 50 mM Tris.HCl, pH 7.5, 5 mM MgCl$_2$, 0.1 mM ATP and 2 mM DTT with the addition of anti-p21$^{ser}$ antibodies or nonimmune normal rabbit immunoglobulin. These immune complexes were washed and resuspended in GTP binding buffer consisting of 100 mM NaCl, 20 mM Tris.HCl at pH 7.2, 5 mM MgCl$_2$, 1% Triton X-100 and 0.1 mM ATP with the addition of 4-10 $\mu$Ci alpha-labeled $^{32}$P dGTP (0.2-0.52 $\mu$M, 800 Ci/mmol) for 30 minutes at 4° C. Immune complexes were then washed in GTP binding buffer and counted in a liquid scintillation counter. The results are shown in FIG. 5, which is a graph of % binding of GTP to the p21 protein for each type of antibody versus a control (with no added antibody) as a function of the concentration of each antibody. Data points represent the means of five determinations relative to the controls with no added antibody.

After treatment with anti-p21$^{ser}$ antibodies, GTP binding to immunoprecipitated p21 protein was reduced five-fold, while no reduction was seen with the control nonimmune antibody. It appears from these results that the anti-p21$^{ser}$ binding site on the p21 protein overlaps the GTP binding site. An alternative explanation is that the antibody binds at some distance from the GTP binding site and yet alters GTP binding by disturbing the tertiary structure of the protein. The first explanation is more likely because of (1) the finding of Furth et al., supra, that both polyclonal sera and monoclonal antibodies directed against various p21 determinants allow GTP binding and (2) applicants' finding that under mild denaturation conditions, high concentrations (10 mM) of GTP (but not ATP) substantially inhibit the binding of anti-p21$^{ser}$ antibodies to p21 protein. The invention herein is not limited to either explanation.

The results herein address the question of how the alteration of the position 12 amino acid can oncogenically activate p21 protein. The blocking of GTP binding by an antibody that recognizes position 12 strongly suggests that this amino acid is involved in the interaction of p21 with GTP and that alteration of this interaction may directly contribute to the oncogenic potential of the protein.

EXAMPLE 2

Normal rat kidney (NRK) cells transformed by Kirsten sarcoma virus obtained from the ATCC under Accession No. ATCC CCL 163.3 (K-234) as described above were microinjected with anti-p21$^{serine}$ at 5 mg affinity purified antibody per ml solution. Kirsten sarcoma virus transforms the cells by producing p21 with serine at position 12. Twelve hours after injection, injected cells were seen to be morphologically changed, and now resembled normal untransformed NRK cells. Thirty hours later, the cells reverted to their fully transformed state. Non-immune normal rabbit antibody as a control had no effect. Injection of anti-p21$^{serine}$ antibody into cells transformed by p21 with arginine at position 12 also had no effect. This shows that the anti-p21$^{serine}$ antibody inhibits the transformed phenotype, i.e., the known biochemical properties of the protein in vivo, whereas the non-immune, normal antibody does not.

Figure 6:
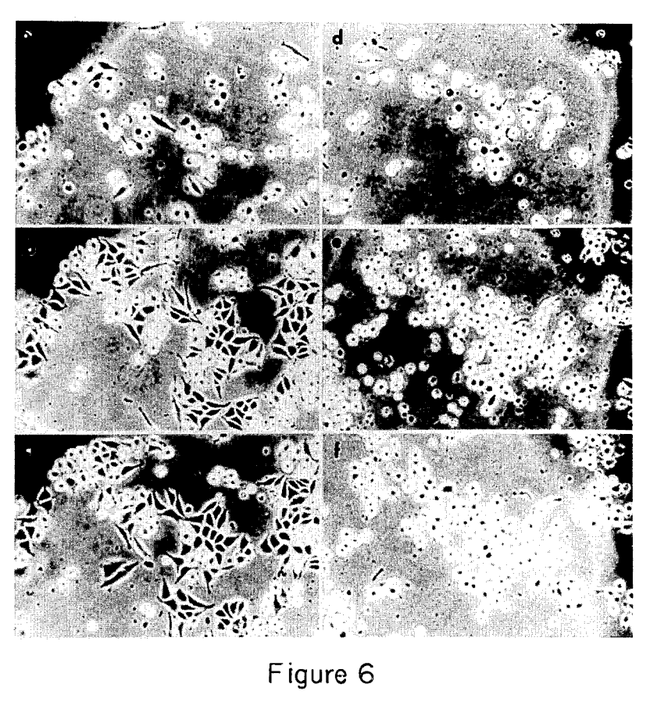

The above microinjection experiment was repeated. In this new experiment the injected cells were seen to be morphologically changed at 24 hours (FIG. 6b) after injection (FIG. 6a represents cells at 0 time). At 36 hours after injection the injected cells were still more changed, resembling normal untransformed flat NRK cells (see FIG. 6c). Normal nonimmune rabbit antibody as a control was found to have no effect on the transformed cells, as shown in FIGS. 6d–6f (with 6d representing 0 time, 6e, 24 hours and 6f, 36 hours). Eventually the cells reverted to their fully transformed state, but they were still alive.

In summary, the present invention is seen to provide anti-peptide antisera (antibodies) which are capable of distinguishing between amino acid substitutions at a single amino acid position of a protein. Therefore, the antibodies can be used to detect the presence of oncogene products responsible for human cancer or for therapeutic applications. The antibodies are prepared by synthesizing certain peptides which will produce the antibodies, e.g., in the anti-p21 antisera, the peptide containing amino acids 5 to 17 of the normal p21 protein, except that at position 12 the glycine is replaced by valine, serine, arginine, cysteine, aspartic acid or alanine, and a cysteine residue was inserted at the penultimate position to the C-terminus. Other peptides would not necessarily produce such antibodies. The protein to be immunoprecipitated with the antibodies is generally partially denatured to expose the epitope of the protein. The antibodies contacted with the protein may be affinity purified to enhance their binding to p21 protein.

Anti-p21$^{ser}$ antibodies were found to immunoprecipitate p21 protein with serine at position 12 and to inhibit quantitatively its autophosphorylation activity. Furthermore, the antibody sharply reduced the ability of p21 v-Ki-ras to bind GTP in a monoclonal antibody immunoabsorption assay. It appears likely, therefore, that the anti-p21$^{ser}$ binding site at position 12 includes a portion of the GTP binding site. These results strongly support the concept that the GTP binding and hydrolysis activities of p21 play a crucial role in the process of oncogenic activation. The anti-p21$^{ser}$ antibody thus may serve as a powerful tool for the study of p21 protein functions in vitro and in vivo.

What is claimed is:

1. A polyclonal antibody preparation that binds selectively to a characteristic marker epitope encompassing amino acid position 12 of an activated form of p21 protein, wherein said polyclonal antibody preparation is specific for a particular amino acid at position 12 and does not bind the p21 protein encoded by the corresponding proto-oncogene.

2. The antibody preparation of claim 1 wherein the amino acid at position 12 is selected from the group consisting of valine, serine, arginine, cysteine, aspartic acid and alanine.

3. The antibody preparation of claim 2 wherein the amino acid is serine.

4. The antibody preparation of claim 1 wherein said antibody is an affinity purified polyclonal antibody.

5. The antibody preparation of claim 1 which is labeled with a detectable label.

6. An immunogenic peptide fragment of the p21 protein which raises the antibody preparation of claim 1 which comprises an amino acid selected from the group consisting of valine, serine, arginine, cysteine, aspartic acid and alanine at position 12 of the p21 protein, an amount of residues flanking position 12 to define the characteristic marker epitope to which the antibody preparation binds selectively, and a cysteine residue in the penultimate position to the C-terminus of the fragment.

7. The peptide fragment of claim 6 comprising amino acids 5 to 17 of the p21 protein with said cysteine residue inserted between amino acids 16 and 17.

8. The peptide fragment of claim 6 conjugated to a carrier protein through the cysteine residue.

9. A method for detecting an activated form of p21 protein in a cellular sample of a patient which protein has a characteristic marker epitope encompassing amino acid position 12 which is not present in the p21 protein encoded by the corresponding proto-oncogene and which is not exposed in the undenatured protein, which method comprises:
   (a) treating the sample with a protein denaturing agent that causes the epitope to be exposed and does not substantially inhibit binding of an antibody to the epitope of said protein,
   (b) incubating the sample with the antibody preparation of claim 5 under conditions that permit the binding of said antibody to said epitope,
   (c) washing the incubated sample to remove unbound labeled antibody, and
   (d) detecting the presence of labeled immune complexes of the epitope and antibody in the incubate.

10. The method of claim 9 wherein the antibody preparation is affinity purified.

11. The peptide fragment of claim 6 of the formula: LYS—LEU—VAL—VAL—VAL—GLY—ALA—X—GLY—VAL—GLY—LYS—CYS—SER, where X is an amino acid selected from the group consisting of valine, serine, arginine, cysteine, aspartic acid, and alanine.

12. The method of claim 9 further comprising the step of incubating the sample with an immobilized polyclonal antibody preparation that binds selectively to said epitope under conditions that permit the binding of said antibody to said epitope, wherein the presence of labeled immobilized immune complexes is detected in the incubate.

13. An inhibiting agent capable of binding selectively to a region of an activated form of p21 protein encoded by an oncogene containing a characteristic marker epitope encompassing amino acid position 12 wherein said polyclonal antibody preparation is specific for a particular amino acid at position 12 and does not bind the p21 protein encoded by the corresponding proto-oncogene, which inhibiting agent has a direct effect on the binding of said p21 protein encoded by said oncogene to a cellular component necessary for the oncogenic activity of said protein encoded by said oncogene.

14. A partially denatured activated form of p21 protein having a characteristic marker epitope encompassing amino acid position 12 that is not exposed in the undenatured protein, which partially denatured p21 protein is characterized by being denatured sufficiently to expose said epitope.

15. A process for preparing the partially denatured protein of claim 14 from an undenatured p21 protein comprising contacting the undenatured p21 protein with a protein denaturing agent under conditions which expose the characteristic marker epitope of the undenatured protein but do not substantially inhibit binding of an antibody to the epitope of said protein.

16. A test kit for conducting an immunometric assay for detecting a characteristic marker epitope encompassing amino acid position 12 of an activated form of p21 protein, comprising, in packaged combination, a multicontainer unit having:
   (a) a container containing a polyclonal antibody preparation that binds selectively to a characteristic marker epitope encompassing amino acid position 12 of an activated form of p21 protein wherein said polyclonal antibody preparation is specific for a particular amino acid at position 12 and does not bind the p21 protein encoded by the corresponding proto-oncogene,
   (b) a container containing a denaturing buffer, and
   (c) a container containing a labeled antibody which binds to the antibody preparation of (a).

17. A test kit for conducting an immunometric assay for detecting a characteristic marker epitope encompassing amino acid position 12 of an activated form of p21 protein, comprising, in packaged combination, a multicontainer unit having:
   (a) a container containing a polyclonal antibody preparation that binds selectively to a characteristic marker epitope encompassing amino acid position 12 of an activated form of p21 protein wherein said polyclonal antibody preparation is specific for a particular amino acid at position 12 and does not bind the p21 protein encoded by the corresponding proto-oncogene,
   (b) a container containing a denaturing buffer.

18. The kit of claim 16 wherein the component (a) antibody preparation is an affinity purified antibody.

19. The kit of claim 17 wherein the antibody preparation is an affinity purified antibody.

20. The kit of claim 17 further comprising:
   (d) a container containing an unlabeled antibody directed against a different epitope than the component (a) antibody and immobilized on a solid support.

21. The kit of claim 20 further comprising a control.

22. The kit of claim 21 wherein the amino acid at position 12 is selected from the group consisting of valine, serine, arginine, cysteine, aspartic acid and alanine.

23. A method for detecting an activated form of p21 protein encoded by an oncogene in a cellular sample of a patient which protein has a characteristic marker epitope encompassing amino acid position 12 which is not present in the p21 protein encoded by the corresponding proto-oncogene and which is not exposed in the undenatured protein, which method comprises:
   (a) treating the sample with a protein denaturing agent that causes the epitope to be exposed and does not substantially inhibit binding of an antibody to the epitope of said protein,
   (b) incubating the sample with the antibody of claim 1 under conditions that permit the binding of said antibody preparation to said epitope,
   (c) incubating the sample with a labeled antibody which binds specifically to the antibody employed in step (b),
   (d) washing the incubated sample to remove unbound labeled antibody, and
   (e) detecting the presence of labeled immune complexes of the epitope with the antibodies employed in steps (b) and (c).

* * * * *